(12) United States Patent
Igarashi et al.

(10) Patent No.: US 8,058,455 B2
(45) Date of Patent: Nov. 15, 2011

(54) COMPOUND SIGNAMYCIN, METHOD FOR PRODUCTION THEREOF, AND USE THEREOF

(75) Inventors: Masayuki Igarashi, Tokyo (JP); Ryutaro Utsumi, Nara (JP)

(73) Assignee: Kinki University, Osaka (JP)

( * ) Notice: Subject to any disclaimer, the term of this patent is extended or adjusted under 35 U.S.C. 154(b) by 0 days.

(21) Appl. No.: 13/033,133

(22) Filed: Feb. 23, 2011

(65) Prior Publication Data

US 2011/0144355 A1    Jun. 16, 2011

Related U.S. Application Data

(63) Continuation of application No. PCT/JP2008/065196, filed on Aug. 26, 2008.

(51) Int. Cl.
*C07D 227/04* (2006.01)
(52) U.S. Cl. .................................. 548/539; 548/544
(58) Field of Classification Search .................. 548/539, 548/544
See application file for complete search history.

(56) References Cited

FOREIGN PATENT DOCUMENTS

| JP | 2004-248596 | 9/2004 |
|---|---|---|
| JP | 2005-523258 | 8/2005 |
| JP | 2006-056787 | 3/2006 |
| WO | 98/09968 | 3/1998 |
| WO | 03/062242 | 7/2003 |

OTHER PUBLICATIONS

Thompson et al. (Genome Biology 2002, 3(7):reviews1020.1-1020.4).*
Tamamura et al. (STN Abstract of JP 06277084 A).*
Okada et al., "Targeting two-component signal transduction: a novel drug discovery system," Methods in Enzymology, 2007. vol. 422. pp. 386-395.
Okada et al., "Isolation of bacterial signal transduction inhibitor by selective isolation method (TS method) and action mechanism of the inhibitor." Proceedings of Annual Meeting of Japan Society for Bioscience, Biotechnology, and Agrochemistry, 2008, vol. 2008, p. 237, lecture No. 3A I 9a10 (English translation provided).
Sievert et al., "Staphylococcus aureus resistant to vancomycin—United States, 2002," Morbidity and Mortality Weekly Report, 2002, vol. 51, pp. 565-567.
Yamamoto et al., "New targets against drug-resistant bacteria, bacterial signal transduction," Bioscience and Industry. 2000, vol. 58, No. 4 (English translation provided).
Fabret et al., "A two-component signal transduction system essential for growth of *Bacillus subtilis*: implications for anti-infective therapy," Journal of Bacteriology, 1998, vol. 180, No. 23, pp. 6375-6383.
Martin et al.. "Role in cell permeability of an essential two-component system in *Staphylococcus aureus*," Journal of Bacteriology, 1999, vol. 181, No. 12. pp. 3666-3673.
Lange et al., "Domain organization and molecular characterization of 13 two-component systems identified by genome sequencing of *Streptococcus pneumonia*," Gene, 1999, vol. 237, pp. 223-234.
Beier et al., "Molecular characterization of two-component systems of helicobacier pylori," 2000. Journal of Bacteriology, vol. 182, No. 8, pp. 2068-2076.
Eriksson et al., Two-component regulators involved in the global control of virulence in *Erwinia carotovora* subsp. carotovora, Molecular Plant-Microbe Interactions, 1998, vol. 11, No. 8, pp. 743-752.
Hyytiainen et al., "The PmrA-PmrB two-component system responding to acidic pH and iron controls virulence in the plant pathogen *Erwinia carotovora* ssp. carotovora," Molecular Microbiology, 2003, vol. 50, No. 3, pp. 795-807.
Flego et al., "A two-component regulatory system, pehR-pehS, controls endopolygalacturonase production and virulence in the plant pathogen *Erwinia carotovora* subsp. carotovora." Molecular Plant-Microbe interactions. 2000. vol. 13, No. 4, pp. 447-455.

* cited by examiner

*Primary Examiner* — Robert Havlin
(74) *Attorney, Agent, or Firm* — Hamre, Schumann, Mueller & Larson, P.C.

(57) ABSTRACT

A compound having a structure expressed by the following Structural Formula (1) and a compound having a structure expressed by the following Structural Formula (2):

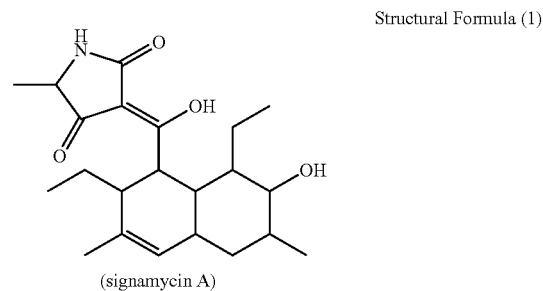

(signamycin A)

Structural Formula (1)

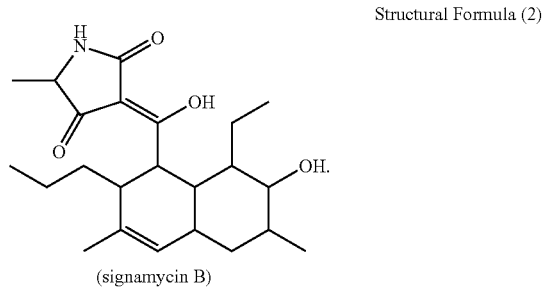

(signamycin B)

Structural Formula (2)

6 Claims, 6 Drawing Sheets

COMPOUND SIGNAMYCIN, METHOD FOR PRODUCTION THEREOF, AND USE THEREOF

CROSS-REFERENCE TO RELATED APPLICATION

This is a continuation application of PCT/JP2008/065196, filed on Aug. 26, 2008.

BACKGROUND OF THE INVENTION

1. Field of the Invention

The present invention relates to a novel compound having an excellent antimicrobial activity against various pathogenic bacteria including drug-resistant bacteria and phytopathogenic bacteria or having an enzyme inhibitory activity against enzymes of the above bacteria, a method for producing the novel compound, use of the novel compound, and a novel microorganism that produces the novel compound.

2. Description of the Related Art

Conventionally, numerous antimicrobial agents have been used as therapeutic drugs for bacterial infectious diseases. Many of the conventionally known antimicrobial agents act on bacteria by inhibiting, for example, their nucleic acid synthesis, protein synthesis and peptide glycan synthesis. Their targeting site is only one, and they mainly aim to inhibit metabolic synthesis pathway. Thus, bacteria that are resistant to these antimicrobial agents easily appear. Particularly in recent years, multidrug resistant bacteria appear that are resistant to a plurality of antibiotics, which is problematic.

For example, as one clinically important problem, *Staphylococcus aureus*, which is known as bacteria causing suppurative diseases, pneumonia and food poisoning, acquires multidrug resistances to methicilline or other antibiotics to be methicilline-resistant *Staphylococcus aureus* (MRSA). At present, vancomycin, teicoplanin, arbekacin, linezolid, etc. are used as typical therapeutic drugs against MRSA. However, it is generally difficult to completely eliminate MRSA. In particular, thorough care should be taken about the use of vancomycin, since appearance of vancomycin resistant *Staphylococcus aureus* (VRSA) has already been reported.

In order to overcome such problems relating to drug-resistant bacteria, demand has arisen for the development of a novel antimicrobial agent that acts on target microorganisms through a new mechanism different from those of the conventional antimicrobial agents (see, for example, Sievert D M, et al: *Staphylococcus aureus* Resistant to Vancomycin-United States, 2002. MMWR Jul. 5, 2002; 51: 565-567).

Meanwhile, bacteria have known to possess signal transduction mechanisms in which receptors respond to and receive changes of the environment and then the expressions of the corresponding genes are controlled. One typical example of the signal transduction mechanisms is two-component systems. The two-component systems are systems that control the expressions of genes responsive to the environment and that are composed of sensor proteins exhibiting histidine kinase activity and regulators which are DNA-binding proteins. Bacteria have various sensors and regulators for responding to various changes in the environment (see, for example, Bioscience and industry, Vol. 58, No. 4).

Such two-component systems of bacteria are, for example, signal transduction mechanisms of Gram-positive bacteria involving YycF and YycG. As has been known, bacteria are killed by inhibiting the actions of YycF and YycG (see, for example, Fablet, C. and Hoch, A. A., J. Bacteriol., 180, 6375-6383, 1998; Marti, P. K., Li, T., Sun, D., Biek, D. P. and Schmid, M. B., J. Bacteriol., 181, 3666-3673, 1999; Lange, R., Wagner, C., DeSaizieu, A., Flint, N., Monos, J., Stiger, M., Caspers, P., Kamber, M., Keck wolfgang, Amrein, K. E., Gene, 237, 223-234, 1999; and Beier, D. and Frank, R., J. Bacteriol., 182, 2068-2076, 2000). Thus, a promising antimicrobial agent is one having antimicrobial activity against Gram-positive bacteria by inhibiting the above signal transduction mechanism.

Also, the pathogenicity of soft-rot bacteria, which infect agricultural crops (e.g., Chinese cabbages and potatoes) to cause severe damage to agricultural production, is known to be controlled by three two-component systems: PehS/PehR (see, for example, Eriksson, A. R. B., Andersson, R. A., Pirhonen, M., and Palva, E. T., Mol. Plant-Microbe Interact., 11, 743-752, 1998), PmrB/PmrA (see, for example, Hyytiainen, H., Sjoblom, S., Palomaki, T., Tuikkala, A., and Palva, E. T., Mol. Microbiol., 50, 795-807, 2003) and ExpS/ExpA (see, for example, Flego, D., Marits, R., Eriksson, A. R. B., Koiv, V., Karlsson, M.-B., Heikinheimo, R., and Palva, E. T., Mol. Plant-Microbe Interact., 13, 447-455, 2000). Thus, prevention/removal of soft-rot bacteria could be satisfactorily achieved by suppressing the pathogenicity.

Although the above-described findings have been obtained, satisfactory antimicrobial agents and enzyme activity inhibitors have not yet been obtained. Demand has presently arisen for the development of excellent antimicrobial agents, etc.

BRIEF SUMMARY OF THE INVENTION

The present invention has been made considering the above-described prior arts and aims to achieve the following objects. That is, an object of the present invention is to provide a novel compound having excellent antimicrobial activity against various pathogenic bacteria including drug-resistant bacteria and phytopathogenic bacteria by inhibiting their two-component systems or having an enzyme inhibitory activity against enzymes of the above bacteria, a method for producing the novel compound, a novel microorganism that produces the novel compound, a compound-containing composition, and an antimicrobial agent and enzyme activity inhibitor each utilizing the novel compound.

In order to solve the above existing problems, the present inventors conducted extensive studies on two-component systems; i.e., main signal transduction mechanisms of bacteria, and have found that they successfully isolate a bacterial strain belonging to the genus *Streptomyces* as a novel microorganism and that the bacterial strain produces compounds each having a novel structural skeleton and having an antimicrobial activity or enzyme inhibitory activity. The present inventors analyzed the chemical structures of these compounds and confirmed that they are novel compounds. On the basis of the findings, the present invention has been completed. Notably, the present inventors named these novel compounds "signamycin A" and "signamycin B."

The present invention is based on the findings obtained by the present inventors. Means for solving the existing problems are as follows.

<1> A compound having a structure expressed by the following Structural Formula (1):

Structural Formula (1)

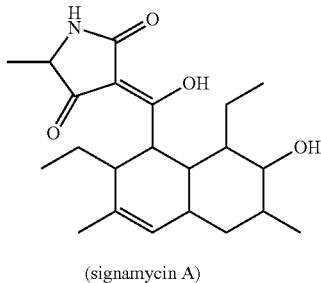

(signamycin A)

<2> A compound having a structure expressed by the following Structural Formula (2):

Structural Formula (2)

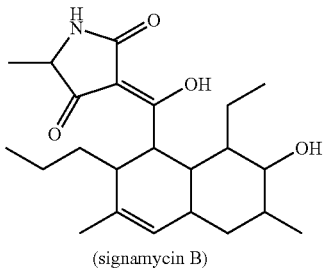

(signamycin B)

<3> A method for producing at least one of the compounds according to <1> and <2>, including:
culturing a microorganism belonging to the genus *Streptomyces* and capable of producing the at least one of the compounds according to <1> and <2>, and
recovering the at least one of the compounds according to <1> and <2> from a culture obtained from the culturing.
<4> The method according to <3>, wherein the microorganism is a microorganism of *Streptomyces* sp. MK851-mF8 strain deposited under accession number NITE BP-612.
<5> A microorganism,
wherein the microorganism belongs to the genus *Streptomyces* and is capable of producing at least one of the compounds according to <1> and <2>.
<6> The microorganism according to <5>, wherein the microorganism is a microorganism of *Streptomyces* sp. MK851-mF8 strain deposited under accession number NITE BP-612.
<7> A composition including:
at least one of the compounds according to <1> and <2>.
<8> An antimicrobial agent including:
at least one of the compounds according to <1> and <2>.
<9> An enzyme activity inhibitor including:
at least one of the compounds according to <1> and <2>.
<10> The enzyme activity inhibitor according to <9>, wherein the enzyme activity inhibitor inhibits histidine kinase activity.

The present invention can provide a novel compound having excellent antimicrobial activity against various pathogenic bacteria including drug-resistant bacteria and phytopathogenic bacteria by inhibiting their two-component systems or having an enzyme inhibitory activity against enzymes of the above bacteria, a method for producing the novel compound, a novel microorganism that produces the novel compound, a compound-containing composition, and an antimicrobial agent and an enzyme activity inhibitor each utilizing the novel compound.

DETAILED DESCRIPTION OF THE INVENTION

Compound

—Compound Having a Structure Expressed by Structural Formula (1)—
One of the compounds of the present invention has a structure expressed by the following Structural Formula (1). The compound having Structural Formula (1) is a novel compound separated by the present inventors (hereinafter may be referred to as "signamycin A").

Structural Formula (1)

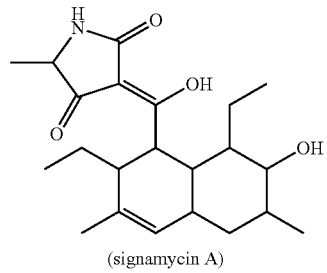

(signamycin A)

Figure 1:
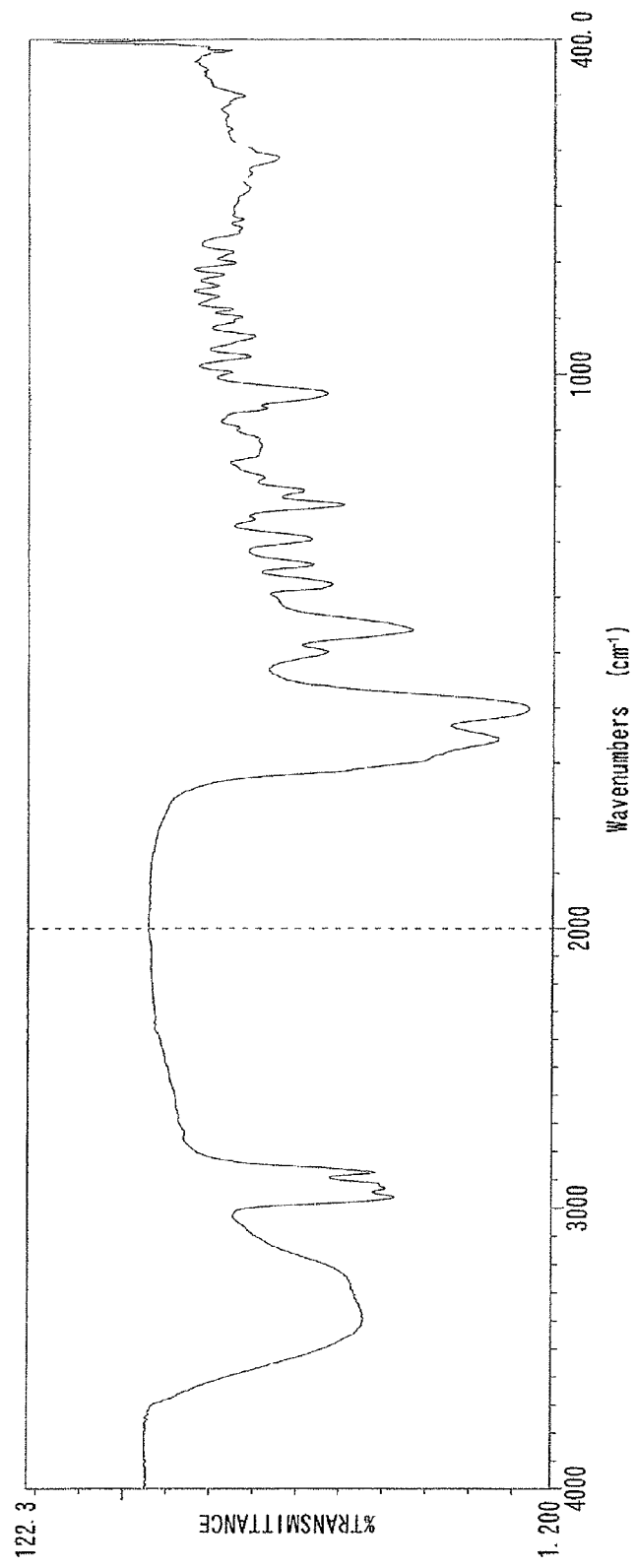
FIG. 1 is an infrared spectrum chart of signamycin A measured by the KBr tablet method (vertical axis: transmittance (%), horizontal axis: wavenumber ($cm^{-1}$)).

—Physico-Chemical Properties—
Physico-chemical properties of the compound having Structural Formula (1) are as follows.
(1) Appearance: colorless powder
(2) Molecular formula: $C_{22}H_{33}NO_4$
(3) Mass spectrum (HRESI):
Calcd: 398.2302 (as $C_{22}H_{33}NO_4Na$)
Found: 398.2296 $(M+Na)^+$
(4) Specific optical rotation: $[\alpha]_D^{20}=+65.74°$ (c=0.46, MeOH)
(5) Infrared absorption spectrum:
$\nu_{max}$ (KBr) $cm^{-1}$: 3500-3200, 2963, 2873, 1689, 1655, 1603, 1458, 1377, 1340, 1294, 1234, 1207, 1034
FIG. 1 is an infrared spectrum chart of signamycin A measured by the KBr tablet method.

Figure 2:
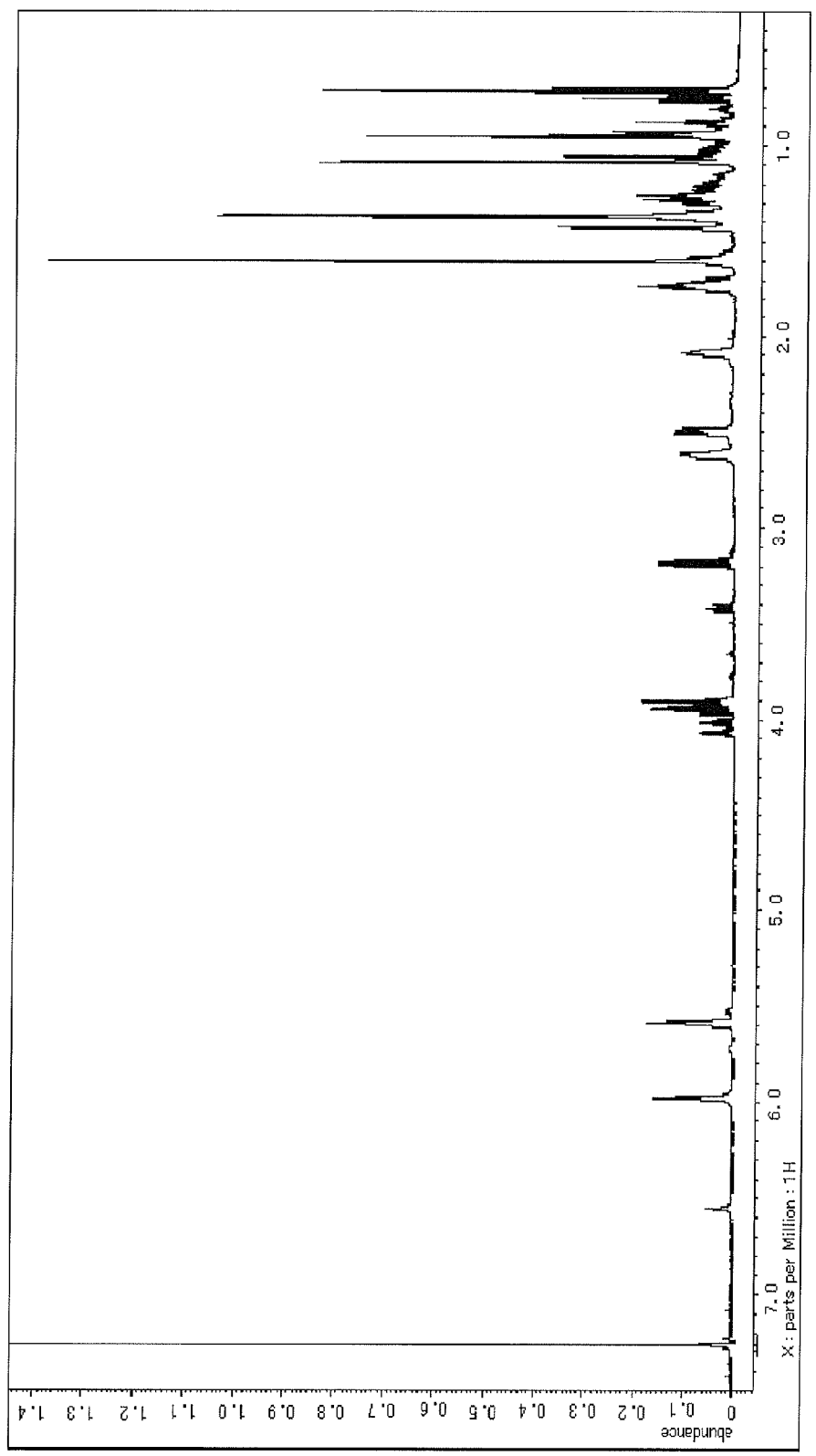
FIG. 2 is a proton nuclear magnetic resonance spectrum chart of signamycin A measured in deuterated chloroform at 30° C. and 600 MHz (the unit of the horizontal axis: ppm).
Figure 3:
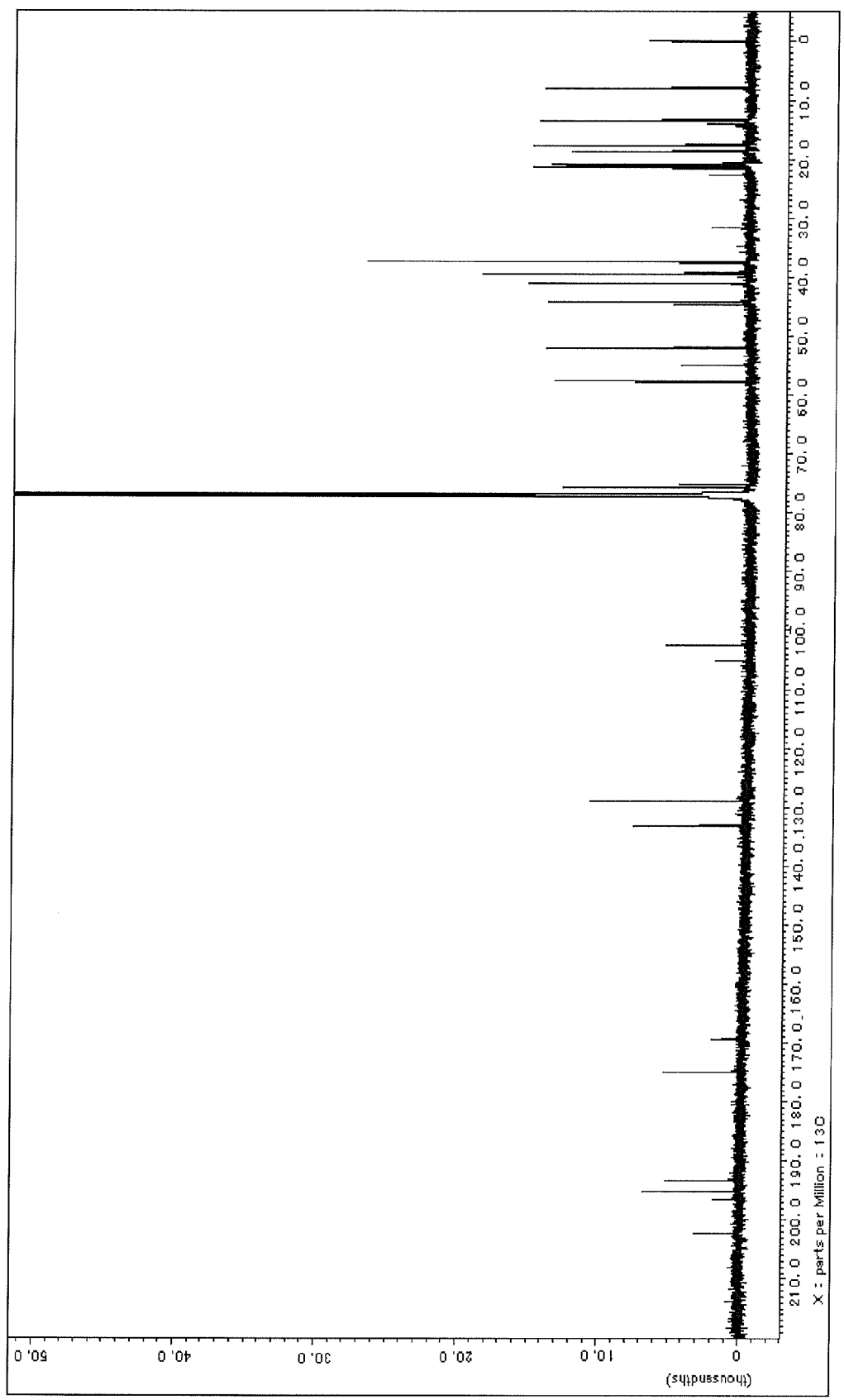
FIG. 3 is a C13 nuclear magnetic resonance spectrum chart of signamycin A measured in deuterated chloroform at 30° C. and 150 MHz (the unit of the horizontal axis: ppm).

(6) UV absorption spectrum:
The UV absorption peaks of signamycin A in methanol are as follows.
$\lambda_{max}$ nm ($\epsilon$)
0.005 M HCl: 221 (sh), 285 (12,300)
0.005 M NaOH: 243 (9,500), 285 (13,000)
(7) Proton nuclear magnetic resonance spectrum:
FIG. 2 is a proton nuclear magnetic resonance spectrum chart of signamycin A measured in deuterated chloroform at 30° C. and 600 MHz.
(8) C13 nuclear magnetic resonance spectrum:
FIG. 3 is a C13 nuclear magnetic resonance spectrum chart of signamycin A measured in deuterated chloroform at 30° C. and 150 MHz.

Whether a compound has a structure expressed by Structural Formula (1) can be determined with appropriately selected various analysis methods. This determination can be performed through, for example, mass spectrum analysis, infrared absorption spectrum analysis, UV absorption spectrum analysis, proton nuclear magnetic resonance spectrum analysis and C13 nuclear magnetic resonance spectrum analysis, as described above.

Notably, signamycin A has tautomerism and thus encompasses its tautomers. Non-limiting examples of the tautomers of signamycin A include those having the following four Structural Formulas. Signamycin A can have such several different structures, and is not considered that it exists at a certain fixed state.

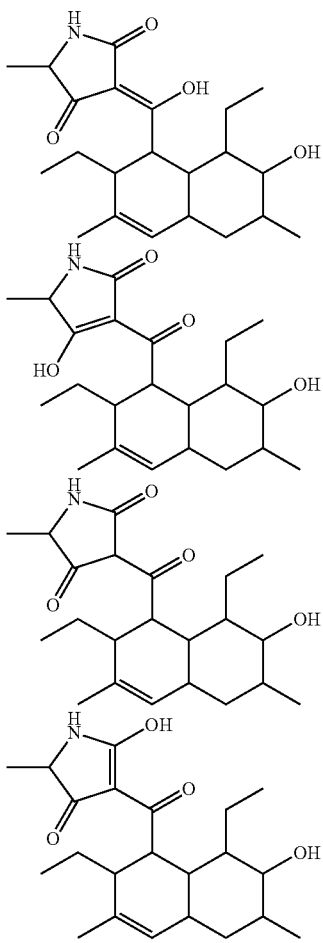

The spectrum charts of signamycin A obtained through proton nuclear magnetic resonance spectrum analysis, C13 nuclear magnetic resonance spectrum analysis, etc. may be somewhat different from those shown in FIGS. 2 and 3. Here, those skilled in the art can easily understand that the compound having Structural Formula (1) can have several different structures actually and does not exist at a certain fixed state. Thus, those skilled in the art could easily identify, as signamycin A, compounds each having a proton nuclear magnetic resonance spectrum chart different from that of FIG. 2, a C13 nuclear magnetic resonance spectrum chart different from that of FIG. 3, and other different spectrum charts.

—Compound Having a Structure Expressed by Structural Formula (2)—

The other compound of the present invention has a structure expressed by the following Structural Formula (2). The compound having Structural Formula (2) is a novel compound insolated by the present inventors (hereinafter may be referred to as "signamycin B").

Structural Formula (2)

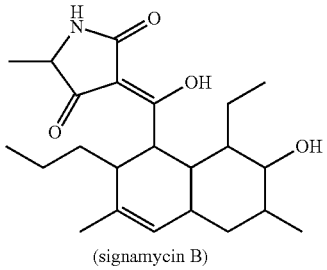

(signamycin B)

Figure 4:
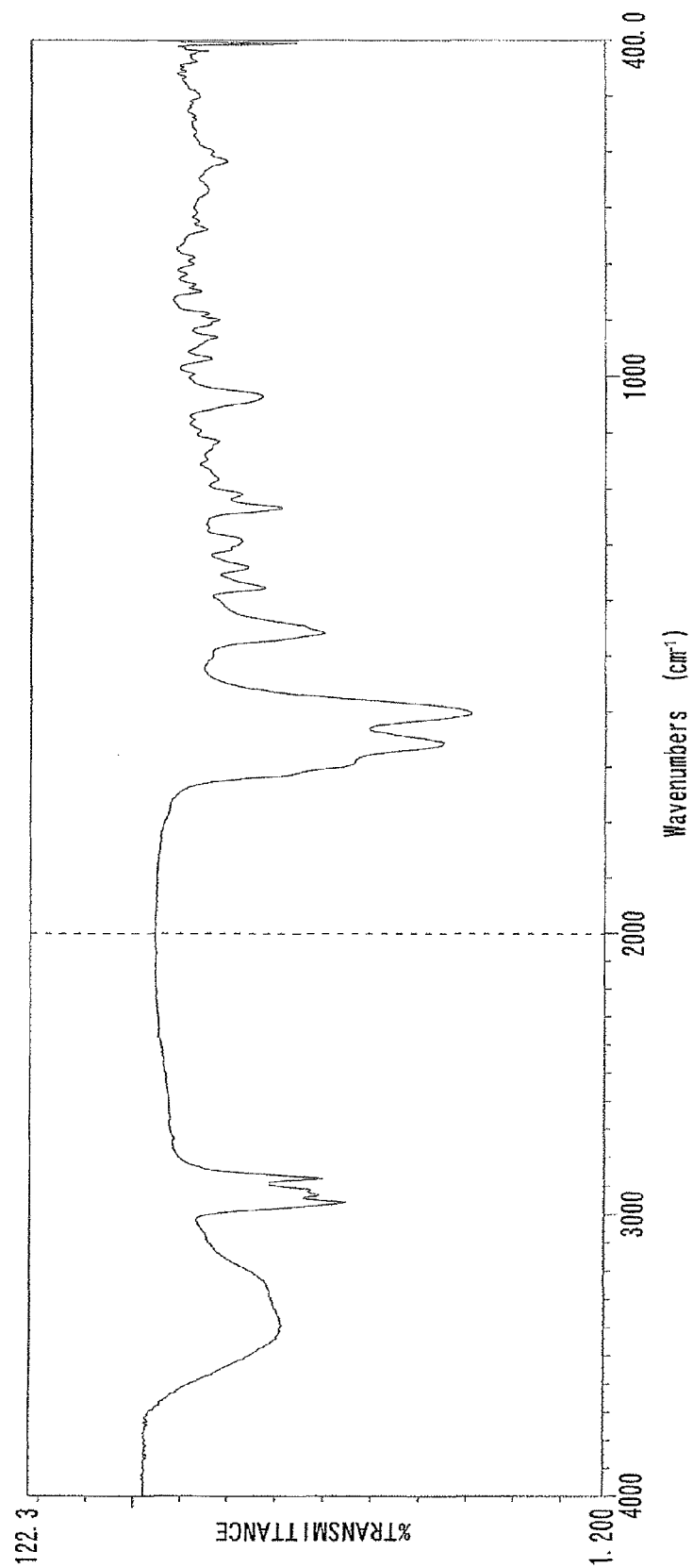
FIG. 4 is an infrared spectrum chart of signamycin B measured by the KBr tablet method (vertical axis: transmittance (%), horizontal axis: wavenumber ($cm^{-1}$)).
Figure 5:
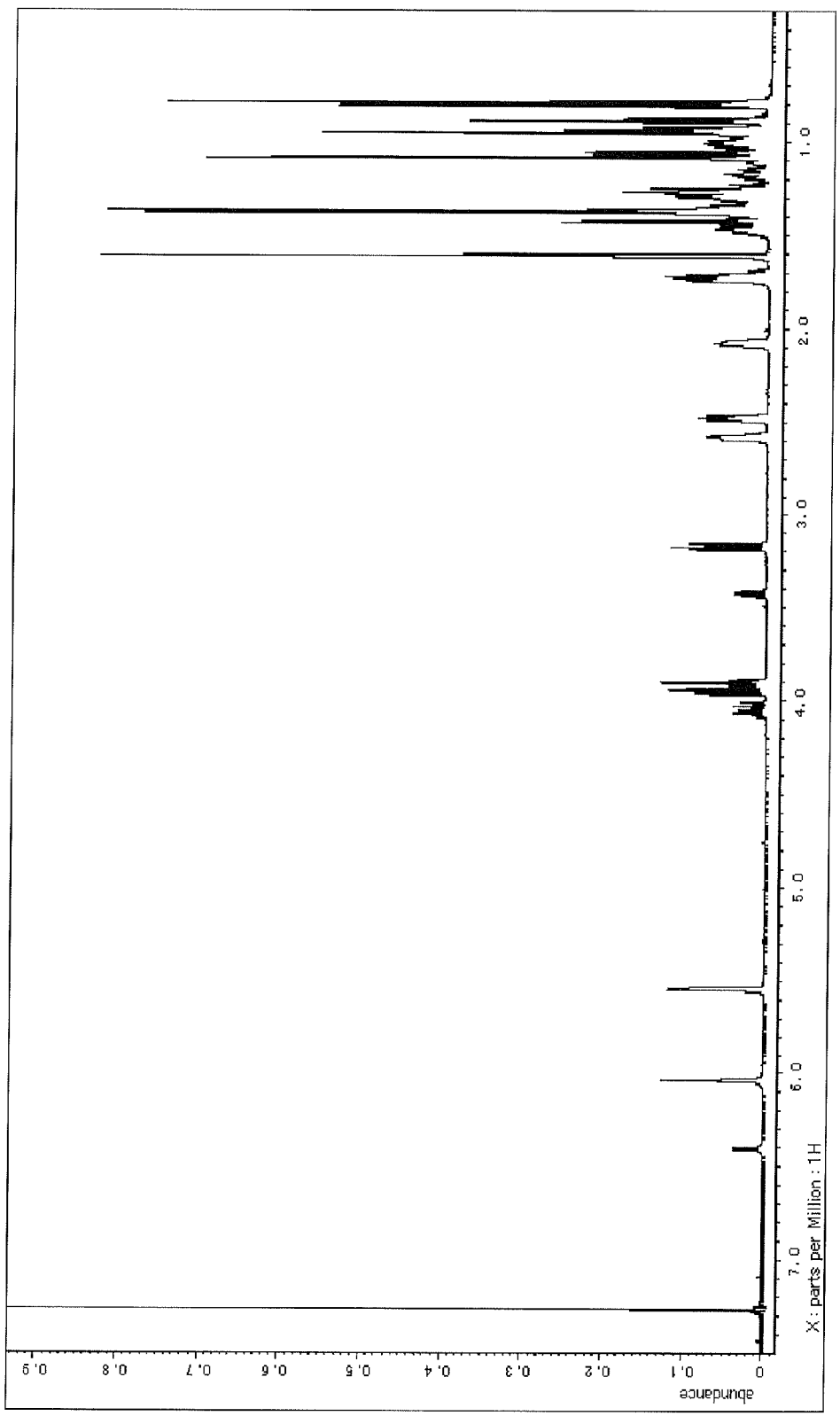
FIG. 5 is a proton nuclear magnetic resonance spectrum chart of signamycin B measured in deuterated chloroform at 30° C. and 600 MHz (the unit of the horizontal axis: ppm).
Figure 6:
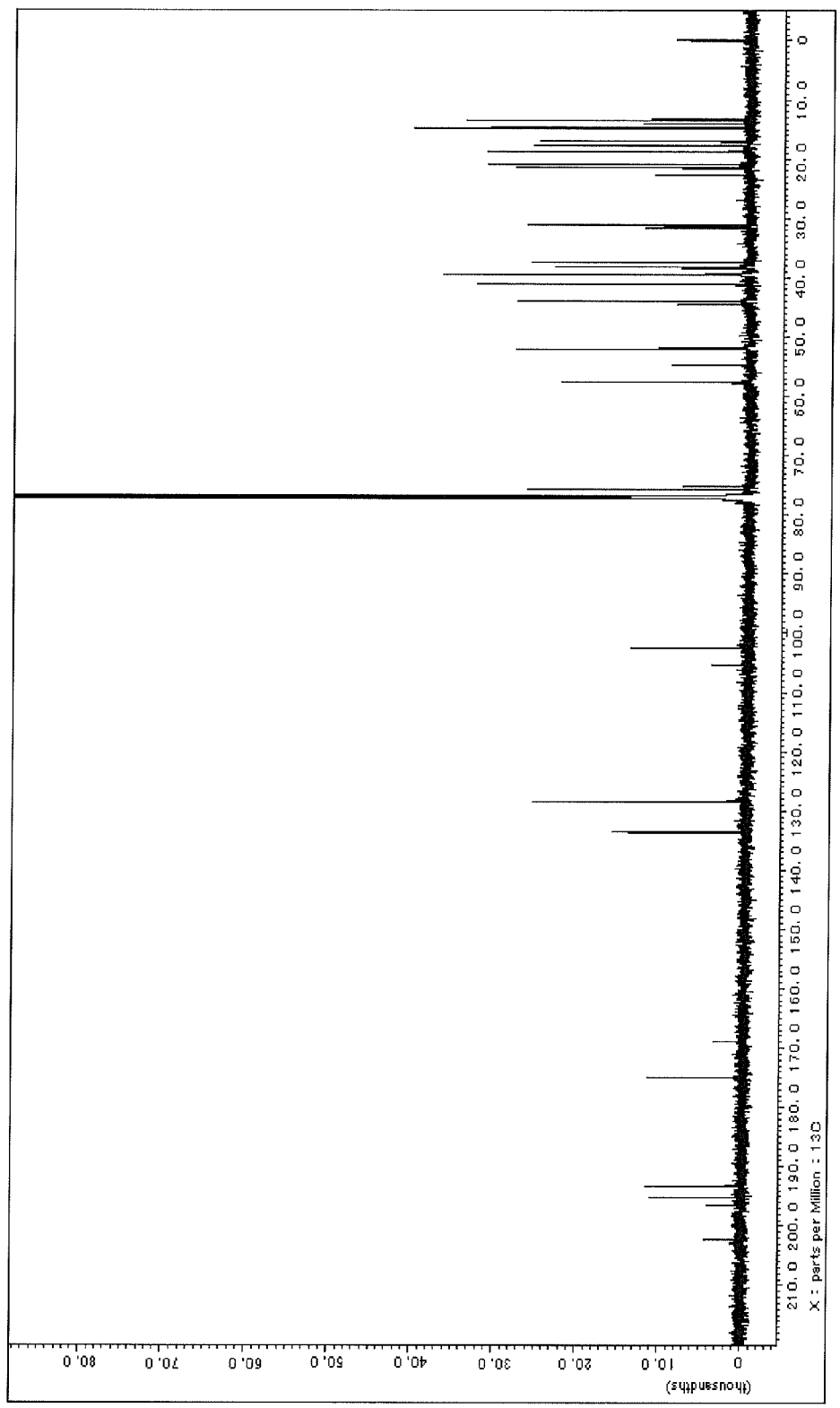
FIG. 6 is a C13 nuclear magnetic resonance spectrum chart of signamycin B measured in deuterated chloroform at 30° C. and 150 MHz (the unit of the horizontal axis: ppm).

—Physico-Chemical Properties—
Physico-chemical properties of the compound having Structural Formula (2) are as follows.
(1) Appearance: colorless powder
(2) Molecular formula: $C_{23}H_{35}NO_4$
(3) Mass spectrum (HRESI):
Calcd: 412.2458 (as $C_{23}H_{35}NO_4Na$)
Found: 412.2456 (M+Na)$^+$
(4) Specific optical rotation: $[\alpha]_D^{20}$=+66.40° (c=0.42, MeOH)
(5) Infrared absorption spectrum:
$\nu_{max}$ (KBr) cm$^{-1}$: 3500-3200, 2956, 2871, 1697, 1655, 1603, 1458, 1377, 1338, 1292, 1232, 1209, 1034
FIG. 4 is an infrared spectrum chart of signamycin B measured by the KBr tablet method.
(6) UV absorption spectrum:
The UV absorption peaks of signamycin B in methanol are as follows.
$\lambda_{max}$ nm ($\epsilon$)
0.005 M HCl: 222 (sh), 285 (11,700)
0.005 M NaOH: 243 (9,500), 284 (13,000)
(7) Proton nuclear magnetic resonance spectrum:
FIG. 5 is a proton nuclear magnetic resonance spectrum chart of signamycin B measured in deuterated chloroform at 30° C. and 600 MHz.
(8) C13 nuclear magnetic resonance spectrum:
FIG. 6 is a C13 nuclear magnetic resonance spectrum chart of signamycin A measured in deuterated chloroform at 30° C. and 150 MHz.

Whether a compound has a structure expressed by Structural Formula (2) can be determined with a method appropriately selected from various analysis methods. This determination can be performed through, for example, mass spectrum analysis, infrared absorption spectrum analysis, UV absorption spectrum analysis, proton nuclear magnetic resonance spectrum analysis and C13 nuclear magnetic resonance spectrum analysis, as described above.

Notably, signamycin B has tautomerism and thus encompasses its tautomers. Non-limiting examples of the tautomers of signamycin B include those having the following four Structural Formulas. Signamycin B can have such several different structures, and is not considered that it exists at a certain fixed state.

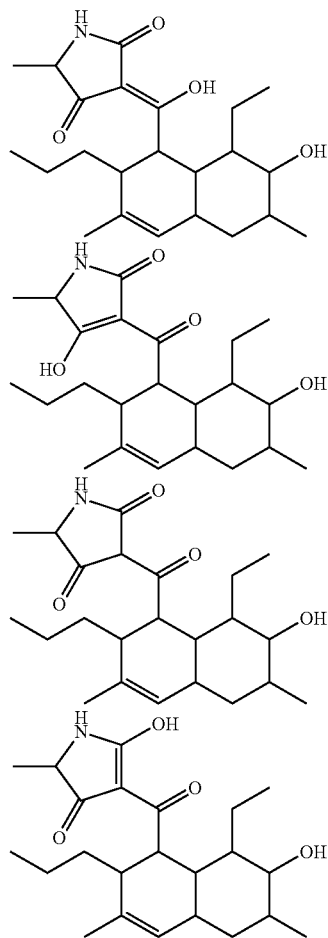

The spectrum charts of signamycin B obtained through proton nuclear magnetic resonance spectrum analysis, C13 nuclear magnetic resonance spectrum analysis, etc. may be somewhat different from those shown in FIGS. 5 and 6. Here, those skilled in the art can easily understand that the compound having Structural Formula (2) can have several different structures actually and does not exist at a certain fixed state. Thus, those skilled in the art could easily identify, as signamycin B, compounds each having a proton nuclear magnetic resonance spectrum chart different from that of FIG. 5, a C13 nuclear magnetic resonance spectrum chart different from that of FIG. 6, and other different spectrum charts.

Signamycin A may be obtained using signamycin A-producing microorganisms or obtained through chemical synthesis. In particular, signamycin A is preferably obtained with the below-described method of the present invention. Similarly, signamycin B may be obtained using signamycin B-producing microorganisms or obtained through chemical synthesis. In particular, signamycin B is preferably obtained with the below-described method of the present invention.

As shown in the below-described Test Examples 1 and 2, signamycin A and signamycin B both have an excellent antimicrobial activity against Gram-positive bacteria, and also have an excellent enzyme inhibitory activity against enzymes of Gram-positive and Gram-negative bacteria. Thus, signamycin A and signamycin B can be suitably used as an active ingredient of, for example, the below-described composition, antimicrobial agent or enzyme activity inhibitor of the present invention.

(Method for Producing Compounds)

A method for producing the compounds of the present invention; i.e., "signamycin A" and "signamycin B," includes at least a culturing step and a recovering step; and, if necessary, further include other steps.

—Culturing Step—

The culturing step is a step of culturing a microorganism belonging to the genus *Streptomyces* and capable of producing at least one of "signamycin A" and "signamycin B."

The microorganism is not particularly limited, so long as it belongs to the genus *Streptomyces* and is capable of producing at least one of "signamycin A" and "signamycin B," and may be appropriately selected depending on the intended purpose. Examples thereof include a microorganism of *Streptomyces* sp. MK851-mF8 strain isolated by the present inventors (NITE BP-612, details will be described in the below "Microorganism" section). Also, other strains that are capable of producing at least one of "signamycin A" and "signamycin B" can be routinely isolated from the natural world. Notably, through mutation treatments such as exposure to radiation, the microorganisms of *Streptomyces* sp. MK851-mF8 strain and other microorganisms capable of producing at least one of "signamycin A" and "signamycin B" can be mutated so that they have increased production capability of at least one of "signamycin A" and "signamycin B." Moreover, at least one of "signamycin A" and "signamycin B" can be produced through genetically engineering techniques.

The culturing at the culturing step is performed as follows. Specifically, microorganisms that produce at least one of "signamycin A" and "signamycin B" (hereinafter may be referred to simply as "signamycin-producing microorganisms") are inoculated into a nutrient medium and cultured at a temperature suitable for the production of at least one of "signamycin A" and "signamycin B."

The nutrient medium is not particularly limited and may be appropriately selected depending on the intended purpose. Examples of the nutrient medium employable include known nutrient media that are conventionally used for culturing actinomycetes.

The nutrient sources added to the nutrient medium are not particularly limited and may be appropriately selected depending on the intended purpose. The nitrogen source may be, for example, commercially available soy flour, peptone, yeast extract, meat extract, corn steep liquor and ammonium sulfate. The carbon source may be, for example, fats and carbohydrates such as tomato paste, glycerin, starch, glucose, galactose and dextrin. In addition, inorganic salts such as a salt and calcium carbonate may be added to the medium before use. If necessary, a trace amount of a metal salt may be added to the medium before use.

Any known materials for culture may be used so long as the signamycin-producing microorganisms can utilize them to produce at least one of "signamycin A" and "signamycin B."

The seed culture used for the production of at least one of "signamycin A" and "signamycin B" is not particularly limited and may be appropriately selected depending on the intended purpose. For example, there can be used the growth culture obtained through slant culturing of signamycin-producing bacteria on an agar medium.

The culturing method at the culturing is not particularly limited and may be appropriately selected depending on the intended purpose. Aerobic culturing is preferred.

The temperature at the culturing is not particularly limited and may be determined depending on the type of the signamycin-producing microorganisms, so long as the growth of the signamycin-producing microorganisms is not substantially inhibited and the signamycin-producing microorganisms can produce at least one of "signamycin A" and "signamycin B." The temperature is preferably 25° C. to 35° C.

The culturing period is not particularly limited and may be appropriately determined in consideration of the amount of at least one of "signamycin A" and "signamycin B" accumulated. In general, the amount of at least one of "signamycin A" and "signamycin B" accumulated becomes maximal for a culturing period of 3 days to 10 days.

—Recovering Step—

The recovering step is a step of recovering at least one of "signamycin A" and "signamycin B" from a culture obtained from the culturing.

"Signamycin A" and "signamycin B" have the above-described physico-chemical properties and thus, can be recovered from the culture utilizing these properties.

The recovering method is not particularly limited and may be appropriately selected from methods that are used for recovering metabolites produced by microorganisms. Examples of the methods include a method by extracting with a water-immiscible solvent, a method utilizing differences in adsorption affinity to various adsorbents, gel filtration, chromatography utilizing countercurrent distribution and combinations thereof.

The separated microorganisms are treated with an extracting method using an appropriate organic solvent or an eluting method through disruption, whereby "signamycin A" and "signamycin B" can be extracted from the microorganisms and isolated/purified as described above.

The production method can be performed as described above. With this production method, "signamycin A" and "signamycin B" can be obtained.

(Microorganism)

A microorganism of the present invention belongs to the genus *Streptomyces* and can produce the above-described compounds of the present invention; i.e., at least one of signamycin A and signamycin B. The microorganism is not particularly limited and may be appropriately selected depending on the intended purpose, so long as it can produce at least one of signamycin A and signamycin B, and thus can be used in the above-described production method of the present invention as the microorganism capable of producing at least one of signamycin A and signamycin B.

In particular, preferably used is *Streptomyces* sp. isolated from the soil of Meguro-ku, Tokyo and given accession number MK851-mF8 strain in September, 1997 by the microbial chemistry research center of Microbial Chemistry Research Foundation. The mycological characteristics of the MK851-mF8 strain are as follows.

1. Morphology

The MK851-mF8 strain extends relatively long aerial hyphae from branched substrate hyphae, the tips of the aerial hyphae being spiraled 8 times to 10 times. The mature spore chains each have a string of 10 to 50 oval to cylindrical spores. Each spore has a size of about 0.5 µm to about 0.6 µm×about 0.9 µm to about 1.1 µm, and has a spinous surface. Whorls, mycelial strands, sporangia and motile spores are not observed.

2. Growth Conditions in Various Media

The standards in blankets relating to colors are based on the color harmony manual of Container Corporation of America.

(1) Yeast-Malt Agar Medium (ISP-Medium 2, Culturing at 27° C.)

This strain is grown in reddish brown [7 pi, Dk Wine], forms aerial hyphae of light brownish gray [4 ge, Lt Fawn] and produces reddish brown soluble dyes. The color in growth and the soluble dyes are changed to dull reddish violet by the addition of 0.1 mol hydrochloric acid but are not changed by the addition of 0.1 mol sodium hydroxide.

(2) Oatmeal Agar Medium (ISP-Medium 3, Culturing at 27° C.)

This strain is grown in grayish, yellowish brown [3 ni, Clove Brown], slightly forms aerial hyphae of grayish white [b, Oyster White] and produces slightly grayish red soluble dyes.

(3) Starch-Inorganic Salt Agar Medium (ISP-Medium 4, Culturing at 27° C.)

This strain is grown in dull yellow [2 ne, Mustard Gold], forms aerial hyphae of yellowish gray [2 ca, Lt Ivory] to light gray [d] and produces pale yellowish orange soluble dyes. The color in growth and the soluble dyes are not changed by the addition of 0.1 mol hydrochloric acid or 0.1 mol sodium hydroxide.

(4) Glycerin-Asparagin Agar Medium (ISP-Medium 5, Culturing at 27° C.)

This strain is grown in dull yellow [2 ne, Mustard Gold to 3 ne, Topaz], slightly forms yellowish white aerial hyphae and produces pale red soluble dyes.

(5) Tyrosine Agar Medium (ISP-Medium 7, Culturing at 27° C.)

This strain is grown in yellowish brown [3 ng, Yellow Maple to 3 pi, Golden Brown], slightly forms white aerial hyphae and produces brown soluble dyes.

(6) Sucrose-Nitrate Agar Medium (Culturing at 27° C.)

This strain is grown in pale yellow [2 gc, Bamboo], slightly forms white aerial hyphae and does not produce soluble dyes.

3. Physiological Properties (1) Temperature Range of Growth

This strain was cultured on a yeast-starch agar medium (soluble starch: 1.0%, yeast extract: 0.2%, string agar: 2.6%, pH 7.0) at a temperature of 10° C., 20° C., 24° C., 27° C., 30° C., 37° C. or 50° C. As a result, the strain was not grown at 10° C. or 50° C. but was grown at 20° C. to 37° C. The optimal growth temperature is about 30° C.

(2) Hydrolysis of Starch (Starch-Inorganic Salt Agar Medium, ISP-Medium 4, Culturing at 27° C.)

On day 5 after culturing, the strain hydrolyzed the starch, exhibiting a moderate degree of hydrolytic activity.

(3) Production of Melanine-Like Dye (Tripton-Yeast-Broth, ISP-Medium 1; Peptone-Yeast-Iron Agar Medium, ISP-Medium 6; Tyrosine Agar Medium, ISP-Medium 7; Culturing at 27° C. on Each Medium)

A melanine-like dye is produced (positive) on the peptone-yeast-iron agar medium and the tyrosine agar medium. Whether it is produced on the tripton-yeast-broth is not clearly determined.

(4) Availability of Carbon Source (Pridham-Godleave Agar Medium, ISP-Medium 9; Culturing at 27° C.)

The strain is grown by utilizing D-glucose, L-arabinose, D-fructose, sucrose, inositol, rhamnose, raffinose and D-mannitol, and may be grown by utilizing D-xylose.

4. Microbial Components 2,6-Diaminopimelic acid contained in the cell wall is one of the LL-form.

5. Analysis of 16S rRNA Gene

A partial nucleotide sequence (1,481 bp) of the 16S rRNA gene was determined and compared with nucleotide sequences of known bacterial strains registered in the DNA database. As a result, the nucleotide sequence of the MK851-mF8 strain was found to have high homology with those of the 16S rRNA genes of actinomycetes belonging to the genus *Streptomyces*; i.e., *Streptomyces canus* (99%), *S. ciscaucasicus* (99%), *S. viridochromogenes* (99%), *S. pseudovenezuelae* (99%), *S. purpureofuscus* subsp. *acoagulans* (99%), *S. resistomycificus* (99%), *S. roseogriseus* (99%), *S. panayensis* (99%), etc. Note that the values in parentheses are homology between the nucleotide sequences.

In summary, the MK851-mF8 strain extends relatively long aerial hyphae from well-branched substrate hyphae in terms of morphology, the tips of the aerial hyphae being spiraled. A string of oval to cylindrical spores is formed. On various media, the strain is grown in dull yellow to reddish brown and forms aerial hyphae of yellowish white to light gray to light brownish gray, and produces red soluble dyes. The optimal growth temperature is about 30° C. The strain is positive in the production of the melanine-like dye, and has a moderate degree of hydrolytic activity of starch.

2,6-Diaminopimelic acid contained in the cell wall of the MK851-mF8 strain is one of the LL-form.

By analyzing a partial nucleotide sequence of the 16S rRNA gene of the MK851-mF8 strain and comparing it with those of known bacterial strains, the sequence has high homology with those of actinomycetes belonging to the genus *Streptomyces*.

In conclusion, the MK851-mF8 strain is thought to belong to the genus *Streptomyces*. Then, the MK851-mF8 is named *Streptomyces* sp. MK851-mF8 strain.

Notably, the MK851-mF8 strain was requested for deposition to National Institute of Technology and Evaluation, Patent Microorganisms Depositary, and was accepted as NITE P-612 on Jul. 23, 2008. The deposit of NITE P-612 was converted to a deposit under the Budapest Treaty on May 6, 2011 under an accession number of NITE BP-612.

Notably, as seen in other bacteria, the MK851-mF8 strain easily changes in its characteristics. The microorganism of the present invention encompasses MK851-mF8 strain-derived mutants (formed as a result of naturally-occurring mutations or inducible mutations), character zygotes, gene recombinants, etc. so long as they are capable of producing at least one of signamycin A and signamycin B. (Compound-containing composition, antimicrobial agent and enzyme activity inhibitor)

—Compound-Containing Composition—

A compound-containing composition of the present invention contains at least one of the above-described compounds of the present invention; i.e., signamycin A and signamycin B; and, if necessary, further contains other ingredients.

The amount of the at least one of signamycin A and signamycin B contained in the compound-containing composition is not particularly limited and may be appropriately selected depending on the intended purpose. Also, the compound-containing composition may be signamycin A or signamycin B itself.

The other ingredients are not particularly limited and may be appropriately selected depending on the intended purpose from, for example, pharmacologically acceptable carriers. Examples of the other ingredients include ethanol, water and starch. The amount of the other ingredients contained in the compound-containing composition is not particularly limited and may be appropriately selected depending on the intended purpose so that the effects of signamycin A or signamycin B are not impaired.

Notably, the compound-containing composition may be used alone or in combination with a drug containing other active ingredients. Also, the compound-containing composition may be incorporated before use into the drug containing other active ingredients.

The compound-containing composition contains at least one of signamycin A and signamycin B, and thus, has at least one of an antimicrobial effect and an enzyme activity inhibitory effect.

—Antimicrobial Agent—

An antimicrobial agent of the present invention contains at least one of the above-described compounds of the present invention; i.e., signamycin A and signamycin B; and, if necessary, further contains other ingredients.

The amount of the at least one of signamycin A and signamycin B contained in the antimicrobial agent is not particularly limited and may be appropriately selected depending on the intended purpose. Also, the antimicrobial agent may be signamycin A or signamycin B itself.

The other ingredients are not particularly limited and may be appropriately selected depending on the intended purpose from, for example, pharmacologically acceptable carriers. Examples of the other ingredients include ethanol, water and starch. The amount of the other ingredients contained in the antimicrobial agent is not particularly limited and may be appropriately selected depending on the intended purpose so that the effects of signamycin A or signamycin B are not impaired.

Notably, the antimicrobial agent may be used alone or in combination with a drug containing other active ingredients. Also, the antimicrobial agent may be incorporated before use into the drug containing other active ingredients.

The antimicrobial agent contains at least one of signamycin A and signamycin B, and thus, has an excellent antimicrobial activity against various Gram-positive bacteria including drug-resistant bacteria as shown in the below-described Test Example 1.

Thus, the antimicrobial agent can be suitably used for preventing or treating infectious diseases caused by drug-resistant bacteria. Also, the antimicrobial agent can be suitably used as a bactericidal agent for agricultural and gardening applications.

—Enzyme Activity Inhibitor—

An enzyme activity inhibitor of the present invention contains at least one of the above-described compounds of the present invention; i.e., signamycin A and signamycin B; and, if necessary, further contains other ingredients.

The enzyme activity inhibitor can effectively inhibit histidine kinase activity.

The amount of the at least one of signamycin A and signamycin B contained in the enzyme activity inhibitor is not particularly limited and may be appropriately selected depending on the intended purpose. Also, the enzyme activity inhibitor may be signamycin A or signamycin B itself.

The other ingredients are not particularly limited and may be appropriately selected depending on the intended purpose from, for example, pharmacologically acceptable carriers. Examples of the other ingredients include ethanol, water and starch. The amount of the other ingredients contained in the enzyme activity inhibitor is not particularly limited and may be appropriately selected depending on the intended purpose so that the effects of signamycin A or signamycin B are not impaired.

Notably, the enzyme activity inhibitor may be used alone or in combination with a drug containing other active ingredients. Also, the enzyme activity inhibitor may be incorporated before use into the drug containing other active ingredients.

The enzyme activity inhibitor contains at least one of signamycin A and signamycin B, and thus, has an excellent enzyme inhibitory activity against enzymes of various Gram-positive and Gram-negative bacteria including drug-resistant bacteria and phytopathogenic bacteria as shown in the below-described Test Example 2.

Thus, the enzyme activity inhibitor can suppress the pathogenicity of various Gram-positive and Gram-negative bacteria including drug-resistant bacteria. Also, the enzyme activity inhibitor can be suitably used for preventing or treating infectious diseases caused by the above bacteria. In addition, the enzyme activity inhibitor can be suitably used as a bactericidal agent for agricultural and gardening applications.

—Dosage Form—

The dosage form of the compound-containing composition, the antimicrobial agent or the enzyme activity inhibitor is not particularly limited and may be appropriately selected depending on the intended purpose. Examples of the dosage form include powder, capsules, tablets and liquids. The compound-containing composition, the antimicrobial agent or the enzyme activity inhibitor can be routinely formed into each of these dosage forms.

Also, when the antimicrobial agent or the enzyme activity inhibitor is used as a bactericidal agent for agriculture and gardening applications, the dosage form thereof is not particularly limited and may be appropriately selected depending on the intended purpose. In general, they can be prepared as appropriate dosage forms through mixing with solid carriers, liquid carriers, surfactants and/or other pharmaceutical aids according to customary formulations. Examples of the appropriate dosage forms include emulsifiable concentrates, soluble powder, liquid preparations, flowables (sols), dusts, granules, fine granules and tablets.

Also, various surfactants (or emulsifiers) are used for forming them into, for example, emulsifiable concentrates, soluble powder, liquid preparations, flowables (sols), dusts, granules, fine granules and tablets. Examples of the surfactant include anionic surfactants (e.g., polyalkyl ethers, polyoxyethylene alkyl esters and polyoxyethylene sorbitan alkyl esters), anionic surfactants (e.g., alkyloxyethylenealkyl sulfates and aryl sulfonates) and cationic surfactants (e.g., alkylamines and polyoxyalkylamines) and amphoteric surfactants (e.g., sulfate ester salts). Needless to say, the surfactants usable in the present invention should not be construed as being limited to the above-exemplified surfactants. Furthermore, various aids can be used which include polyvinyl alcohols, carboxymethyl cellulose, gum arabic, polyvinyl acetate, sodium alginate, gelatin and gum tragacanth.

—Administration—

The administration method of the compound-containing composition, the antimicrobial agent or the enzyme activity inhibitor is not particularly limited and may be appropriately selected depending on, for example, the dosage form of the compound-containing composition, the antimicrobial agent or the enzyme activity inhibitor. The compound-containing composition, the antimicrobial agent or the enzyme activity inhibitor can be administered orally or parenterally.

The dose of the compound-containing composition, the antimicrobial agent or the enzyme activity inhibitor is not particularly limited and may be appropriately determined considering various factors of target individuals such as their age, body weight, constitution, symptoms and concomitant use of a drug containing other active ingredients.

The administration period of the compound-containing composition, the antimicrobial agent or the enzyme activity inhibitor is not particularly limited and may be appropriately determined depending on the intended purpose.

The animal species to which the compound-containing composition, the antimicrobial agent or the enzyme activity inhibitor is administered is not particularly limited and may be appropriately selected depending on the intended purpose. Examples thereof include humans, monkeys, pigs, bovines, sheep, goats, dogs, cats, mice, rats and birds.

Also, when they are used as the bactericidal agent for agriculture and gardening applications, the administration method, the dose, the administration period and the target individuals are not particularly limited and may be appropriately selected depending on the intended purpose.

EXAMPLES

The present invention will next be described in detail by way of Examples and Test Examples, which should not be construed as limiting the present invention thereto. In Examples and Test Examples, the unit "%" means "% by mass" unless otherwise specified.

Example 1

Production of Signamycin A and Signamycin B

—Culturing Step—

Cells of *Streptomyces* sp. MK851-mF8 strain (deposited as NITE BP-612) were cultured in an agar slant medium. Separately, a liquid medium containing galactose 2%, dextrin 2%, glycerin 1%, Bacto Soytone (product of Difco Co., Ltd.) 1%, corn steep liquor 0.5%, ammonium sulfate 0.2% and calcium carbonate 0.2% (the pH of the liquid medium being adjusted to 7.0) was dispensed in 500 mL-conical flasks so that each conical flask contained 110 mL of the liquid medium, followed by routinely sterilizing at 120° C. for 20 min. The above-cultured cells were inoculated in the liquid medium. Thereafter, the cells were shake-cultured through rotation at 30° C. for 4 days, to thereby obtain seed culture liquids.

A liquid medium containing glycerin 0.5%, dextrin 0.5%, Bacto Soytone (product of Difco Co., Ltd.) 0.25%, yeast extract (product of NIHON PHARMACEUTICAL CO., LTD.) 0.075%, ammonium sulfate 0.05% and calcium carbonate 0.05% (the pH of the liquid medium being adjusted to 7.0) was dispensed in 500 mL-conical flasks so that each conical flask contained 110 mL of the liquid medium, followed by routinely sterilizing at 120° C. for 20 min, to thereby obtain production media. Two percent by volume of each seed culture liquid was inoculated in each production media, followed by shake-culturing at 27° C. for 6 days through rotation (180 rpm).

—Recovering Step—

The thus-obtained culture liquid (3 L) was centrifuged so as to be separated into the culture filtrate and the microorganisms. Subsequently, methanol (1 L) of was added to the microorganisms, followed by thoroughly stirring. Then, signamycin A and signamycin B were extracted from the microorganisms with methanol, to thereby obtain a microorganism extract (1.37 L) containing signamycin A and signamycin B. Water (1.37 L) was added to the microorganism extract (1.37 L), followed by thoroughly stirring. The resultant mixture was caused to pass through a Diaion CHP20P (60 mm (inner diameter)×220 mm, product of Mitsubishi Chemical Corporation) column for adsorption. The column was washed with 50% aqueous methanol (1.8 L), and then the active fraction containing signamycin A and signamycin B was eluted with 80% aqueous methanol (1.8 L). The eluted 80% aqueous methanol (1.8 L) was concentrated and dried under reduced pressure, to thereby obtain 0.842 g of a crude product containing signamycin A and signamycin B.

The crude product (0.842 g) containing signamycin A and signamycin B was dissolved in methanol, and the resultant solution was chromatographically separated with a Sephadex LH-20 (26 mm (inner diameter)×480 mm, product of Pharmacia Biotech Inc.) column. The solution was fractionated every 5 g (one fraction) and, as a result, the active fractions were eluted as fractions 23 to 36. The fractions were collected and concentrated/dried under reduced pressure, to thereby obtain 660 mg of a crude product containing signamycin A and signamycin B.

The crude product (660 mg) was dissolved in a small amount of methanol. The resultant solution was subjected to C18 reverse-phase column chromatography (using Capcell pak UG120, 30 mm (inner diameter)×250 mm (length), product of Shiseido Co., Ltd.), to thereby separate signamycin A from signamycin B. Specifically, through chromatography at a flow rate of 15 mL/min using a developing solvent of acetonitrile water trifluoroacetic acid=60:40:0.001, signamycin A was eluted at 33 min to 34 min and signamycin B was eluted at 42 min to 48 min. These eluted products were collected and concentrated/dried under reduced pressure, to thereby obtain 22.5 mg of pure signamycin A and 206.4 mg of pure signamycin B.

Through analysis, the obtained signamycin A was found to have the physico-chemical properties as shown below. From the physico-chemical properties, it was confirmed that signamycin A was a novel compound having a structure expressed by the following Structural Formula (1).

(1) Appearance: colorless powder
(2) Molecular formula: $C_{22}H_{33}NO_4$
(3) Mass spectrum (HRESI):
    Calcd: 398.2302 (as $C_{22}H_{33}NO_4Na$)
    Found: 398.2296 (M+Na)$^+$
(4) Specific optical rotation: $[\alpha]_D^{20}$=+65.74° (c=0.46, MeOH)
(5) Infrared absorption spectrum:
    $v_{max}$ (KBr) cm$^{-1}$: 3500-3200, 2963, 2873, 1689, 1655, 1603, 1458, 1377, 1340, 1294, 1234, 1207, 1034

FIG. 1 is an infrared spectrum chart of signamycin A measured by the KBr tablet method.

(6) UV absorption spectrum:
The UV absorption peaks of signamycin A in methanol are as follows.
$\lambda_{max}$ nm ($\epsilon$)
0.005 M HCl: 221 (sh), 285 (12,300)
0.005 M NaOH: 243 (9,500), 285 (13,000)
(7) Proton nuclear magnetic resonance spectrum:
FIG. 2 is a proton nuclear magnetic resonance spectrum chart of signamycin A measured in deuterated chloroform at 30° C. and 600 MHz.
(8) C13 nuclear magnetic resonance spectrum:
FIG. 3 is a C13 nuclear magnetic resonance spectrum chart of signamycin A measured in deuterated chloroform at 30° C. and 150 MHz.

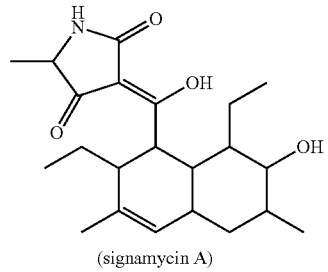

Structural Formula (1)

(signamycin A)

Through analysis, the obtained signamycin B was found to have the physico-chemical properties as shown below. From the physico-chemical properties, it was confirmed that signamycin B was a novel compound having a structure expressed by the following Structural Formula (2).

(1) Appearance: colorless powder
(2) Molecular formula: $C_{23}H_{35}NO_4$
(3) Mass spectrum (HRESI):
    Calcd: 412.2458 (as $C_{23}H_{35}NO_4Na$)
    Found: 412.2456 (M+Na)$^+$
(4) Specific optical rotation: $[\alpha]_D^{20}$=+66.40° (c=0.42, MeOH)
(5) Infrared absorption spectrum:
    $v_{max}$ (KBr) cm$^{-1}$: 3500-3200, 2956, 2871, 1697, 1655, 1603, 1458, 1377, 1338, 1292, 1232, 1209, 1034

FIG. 4 is an infrared spectrum chart of signamycin B measured by the KBr tablet method.

(6) UV absorption spectrum:
The UV absorption peaks of signamycin B in methanol are as follows.
$\lambda_{max}$ nm ($\epsilon$)
0.005 M HCl: 222 (sh), 285 (11,700)
0.005 M NaOH: 243 (9,500), 284 (13,000)
(7) Proton nuclear magnetic resonance spectrum:
FIG. 5 is a proton nuclear magnetic resonance spectrum chart of signamycin B measured in deuterated chloroform at 30° C. and 600 MHz.
(8) C13 nuclear magnetic resonance spectrum:
FIG. 6 is a C13 nuclear magnetic resonance spectrum chart of signamycin A measured in deuterated chloroform at 30° C. and 150 MHz.

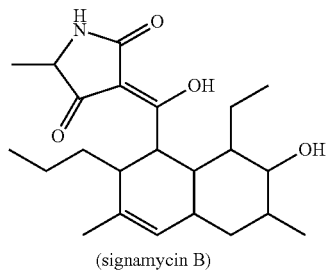

Structural Formula (2)

(signamycin B)

The obtained signamycin A and signamycin B were measured for antimicrobial activity and enzyme inhibitory activity in the following Test Examples 1 and 2.

Test Example 1

Antimicrobial Activity

According to the standard method of Japanese Society of Chemotherapy, signamycin A and signamycin B were measured for antimicrobial spectrum against various microorganisms including drug-resistant bacteria (methicilline resistant bacteria and vancomycin resistant bacteria) on the Muller Hinton agar medium by the multiple dilution method. The minimum inhibitory concentrations (MICs) measured are shown in Table 1.

TABLE 1

| | | MIC (µg/mL) | |
|---|---|---|---|
| Test organisms | Strain | Signamycin A | Signamycin B |
| Staphylococcus aureus | FDA 209P | 4 | 4 |
| S. aureus | Smith | 8 | 4 |
| S. aureus | MS9610 (MDR) | 8 | 4 |
| S. aureus | MRSA No. 5 (MRSA) | 8 | 4 |
| S. aureus | MRSA No. 17 (MRSA) | 8 | 4 |
| S. aureus | MS16526 (MRSA) | 8 | 4 |
| S. aureus | TY-04282 (MRSA) | 8 | 4 |
| Micrococcus luteus | FDA 16 | 8 | 4 |
| M. luteus | IFO 3333 | 8 | 4 |
| M. luteus | PCI 1001 | 8 | 4 |
| Bacillus subtilis | NRRL B-558 | 4 | 4 |
| B. subtilis | PCI 219 | 4 | 4 |
| B. cereus | ATCC 10702 | 4 | 2 |
| Corynebacterium bovis | 1810 | 8 | 8 |
| Escherichia coli | NIHJ | 32 | 64 |
| Mycobacterium smegmatis | ATCC607* | 32 | 64 |
| Enterococcus faecalis | JCM 5803 | 16 | 8 |
| E. faecalis | NCTC 12201 (VRE, vanA) | 16 | 8 |
| E. faecalis | NCTC 12203 (VRE, vanA) | 8 | 8 |
| E. faecium | JCM 5804 | 8 | 8 |
| E. faecium | NCTC 12202 (VRE, vanA) | 16 | 8 |
| E. faecium | NTCTC 12204 (VRE, vanA) | 8 | 8 |
| Pseudomonasu aeruginosa | A3 | >100 | >100 |

Muller Hinton agar, 37° C., 18 hrs.
*37° C. 42 hrs.
VRE: vancomycin resistant Enterococcus,
MDR: multidrug resistant,
MRSA: Methicillin resistant Staphylococcus aureus As shown in Table 1, signamycin A and signamycin B were found to have an antimicrobial activity against Gram-positive bacteria including S. aureus MS9610 (which is multidrug resistant (MDR) Staphylococcus aureus); S. aureus MRSA No. 5, S. aureus MRSA No. 17, S. aureus MS16526 and S. aureus TY-04282 (which are methicilline resistant Staphylococcus aureus (MRSA)); and E. faecalis NCTC 12201, E. faecalis NCTC 12203, E. faecium NCTC 12202 and E. faecium NTCTC 12204 (which are vancomycin resistant Enterococcus (VRE)).

In particular, signamycin A was found to have a high antimicrobial activity against Staphylococcus aureus (S. aureus), and signamycin B was found to have a high antimicrobial activity against Staphylococcus aureus (S. aureus) and Enterococcus (E. faecalis and E. faecium).

Test Example 2

Enzyme Inhibitory Activity

—(1) VicK Histidine Kinase Activity Inhibitory Test—

Signamycin A and signamycin B were measured for enzyme inhibitory activity against VicK of caries bacteria (Streptococcus mutans).

The histidine kinase activity was measured by a modified method of the method reported in Biosci. Biotechnol. Biochem., 64, 919-923, 2000.

A DNA fragment encoding a region containing only the kinase activity domain of VicK (i.e., a region containing the 31th amino acid to the 450th amino acid from the N-terminus) was prepared through PCR from the chromosomal DNA of the caries bacteria, and was cloned into the expression vector pET21a (+). The thus-obtained plasmid pET-SMvicK31-450 was used to transform Escherichia coli cells. The culture liquid of the thus-transformed strain was treated to purify a protein expressing only the histidine kinase activity domain of VicK (VicK-31-450).

The reaction solution having the following formulation was used for measuring histidine kinase activity: 0.5 M VicK-31-450, 50 mM Tris-HCl (pH 7.5), 50 mM KCl and 10 mM $MgCl_2$. Signamycin A or signamycin B (1 µL) was added to the reaction solution (7 µl), followed by incubating at 25° C. for 5 min. Subsequently, 2 µL of 12.5 M ATP containing [$^{32}$P]ATP was added to the reaction mixture (final concentration: 2.5 M) to initiate the reaction, followed by incubating at 25° C. for 20 min. After termination of the reaction, SDS-polyacrylamide gel electrophoresis was performed to determine the 50% inhibitory concentration ($IC_{50}$) with respect to VicK of caries bacteria. The results are shown in Table 2.

—(2) YycG Histidine Kinase Activity Inhibitory Test—

Signamycin A and signamycin B were measured for enzyme inhibitory activity against YycG of Bacillus subtilis 168 strain (B. subtilis 168).

The histidine kinase activity was measured according to the method reported in Biosci. Biotechnol. Biochem., 64, 919-923, 2000.

A DNA fragment encoding a region containing only the kinase activity domain of YycG (i.e., a region containing the 204th amino acid to the 611th amino acid from the N-terminus) was prepared through PCR from the chromosomal DNA of the *Bacillus subtilis* 168 strain, and was cloned into the expression vector pET21a (+). The thus-obtained plasmid pET-yycGtru was used to transform *Escherichia coli* cells. The culture liquid of the thus-transformed strain was treated to purify a protein expressing only the histidine kinase activity domain of YycG (YycG-204-611).

The reaction solution having the following formulation was used for measuring histidine kinase activity: 0.5 µM YycG-204-611, 50 mM Tris-HCl (pH 8.5), 100 mM KCl, 100 mM NH$_4$Cl and 5 mM MgCl$_2$. A 2.5 µM ATP-10 µCi [γ-$^{32}$P] ATP mixture was added to the reaction solution to initiate the reaction so that the total amount was adjusted to 10 µL. The resultant mixture was incubated at 30° C. for 10 min. After termination of the reaction, SDS-polyacrylamide gel electrophoresis was performed. For measuring inhibitory activity, signamycin A or signamycin B was added to the reaction solution before the addition of the ATP mixture so as to have a predetermined concentration, followed by incubating at 30° C. for 5 min, to thereby determine the 50% inhibitory concentration (IC$_{50}$) with respect to YycG of *Bacillus subtilis*. The results are shown in Table 2.

—(3) PehS Histidine Kinase Activity Inhibitory Test—

Signamycin A and signamycin B were measured for enzyme inhibitory activity against PehS of soft-rot bacteria MAFF301393 strain (*Erwinia carotovora* subsp. *carotovora* MAFF301393).

The histidine kinase activity was measured according to the method reported in Biosci. Biotechnol. Biochem., 64, 919-923, 2000.

A DNA fragment encoding a region containing only the kinase activity domain of YycG (i.e., a region containing the 209th amino acid to the 484th amino acid from the N-terminus) was prepared through PCR from the chromosomal DNA of the soft-rot bacteria MAFF301393 strain, and was cloned into the expression vector pET21a (+). The thus-obtained plasmid pET-pehScM2-2 was used to transform *Escherichia coli* cells. The culture liquid of the thus-transformed strain was treated to purify a protein expressing only the histidine kinase activity domain of PehS (PehS-209-484).

The reaction solution having the following formulation was used for measuring histidine kinase activity: 4 µM PehS-209-484, 50 mM Tris-HCl (pH 8.5), 100 mM KCl, 100 mM NH$_4$Cl and 5 mM MgCl$_2$. A 2.5 µM ATP-10 µCi [γ-$^{32}$P] ATP mixture was added to the reaction solution to initiate the reaction so that the total amount was adjusted to 10 µL. The resultant mixture was incubated at 30° C. for 20 min. After termination of the reaction, SDS-polyacrylamide gel electrophoresis was performed. For measuring inhibitory activity, signamycin A or signamycin B was added to the reaction solution before the addition of the ATP mixture so as to have a predetermined concentration, followed by incubating at 30° C. for 5 min, to thereby determine the 50% inhibitory concentration (IC$_{50}$) with respect to PehS of soft-rot bacteria. The results are shown in Table 2.

TABLE 2

| Compounds | IC$_{50}$ (µM) | | |
|---|---|---|---|
| | YycG | VicK | PehS |
| Signamycin A | 137.9 | 239.1 | 33.6 |
| Signamycin B | 43 | 62.2 | 15.7 |

As shown in Table 2, signamycin A and signamycin B were found to have an inhibitory activity against histidine kinases of Gram-positive and Gram-negative bacteria. In particular, signamycin A and signamycin B were found to have a strong inhibitory activity against PehS.

The novel compounds of the present invention (i.e, signamycin A and signamycin B) have an excellent antimicrobial activity against Gram-positive bacteria, and also have an excellent enzyme inhibitory activity against enzymes of Gram-positive and Gram-negative bacteria. Thus, they can be suitably used as a new antimicrobial agent and a new enzyme activity inhibitor.

| | | |
|---|---|---|
| 0-1 | Form PCT/RO/134 (SAFE) Indications Relating to Deposited Microorganism(s) or Other Biological Material (PCT Rule 13bis) | |
| 0-1-1 | Prepared Using | JPO-PAS 0352 |
| 0-2 | International Application No. | |
| 0-3 | Applicant's or agent's file reference | N-BK002-08P |
| 1 | The indications made below relate to the deposited microorganism(s) or other biological material referred to in the description on: | |
| 1-1 | Paragraph number | 0040 |
| 1-3 | Identification of deposit | |
| 1-3-1 | Name of depositary institution | NPMD National Institute of Technology and Evaluation, Patent Microorganisms Depositary |
| 1-3-2 | Address of depositary institution | 2-5-8 Kazusakamatari Kisarazu-city Chiba 292-0818 Japan |
| 1-3-3 | Date of deposition | Jul. 23, 2008 (23. 07. 2008) |
| 1-3-4 | Accession Number | NPMD NITE P-612 |
| 1.5 | Designated States for Which Indications are Made | All designations |

For Receiving Office Use Only

| | | |
|---|---|---|
| 0-4 | This form was received with the international application: | |
| 0-4-1 | Authorized officer | |

For International Bureau Use Only

| 0-5 | This form was received by the international Bureau on: |
|---|---|
| 0-5-1 | Authorized officer |

What is claimed is:

1. A compound having a structure expressed by following Structural Formula (1):

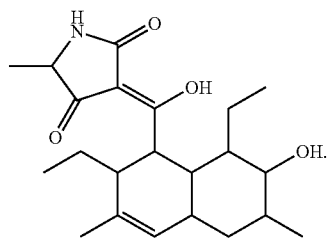

2. A compound having a structure expressed by following Structural Formula (2):

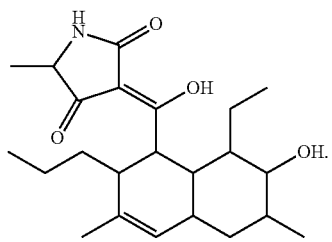

3. A method for producing at least one of a compound having a structure expressed by following Structural Formula (1) and a compound having a structure expressed by following Structural Formula (2), comprising:

culturing a microorganism, which is a strain deposited under an accession number of NITE BP-612, belonging to a genus *Streptomyces* and capable of producing at least one compound selected from the group consisting of Structural Formula (1) and Structural Formula (2); and recovering the at least one of the compound from a culture obtained from the culturing step:

Structural Formula (1)

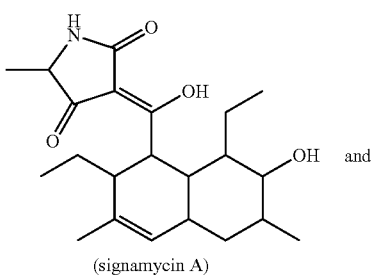

(signamycin A)

Structural Formula (2)

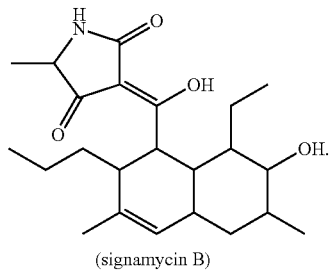

(signamycin B)

4. A composition comprising: at least one of a compound having a structure expressed by the following Structural Formula (1) and a compound having a structure expressed by the following Structural Formula (2):

Structural Formula (1)

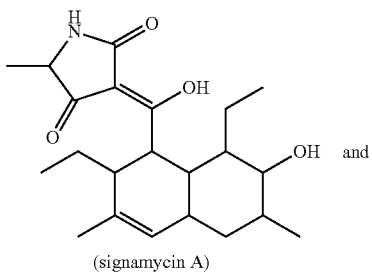

(signamycin A)

Structural Formula (2)

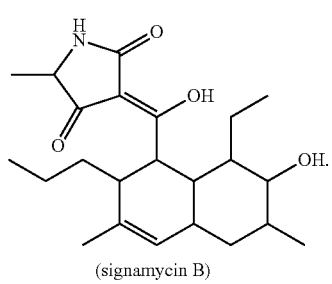

(signamycin B)

5. An antimicrobial agent comprising: at least one compound selected from the group consisting of a compound having a structure expressed by following Structural Formula (1) and a compound having a structure expressed by following Structural Formula (2):

Structural Formula (1)

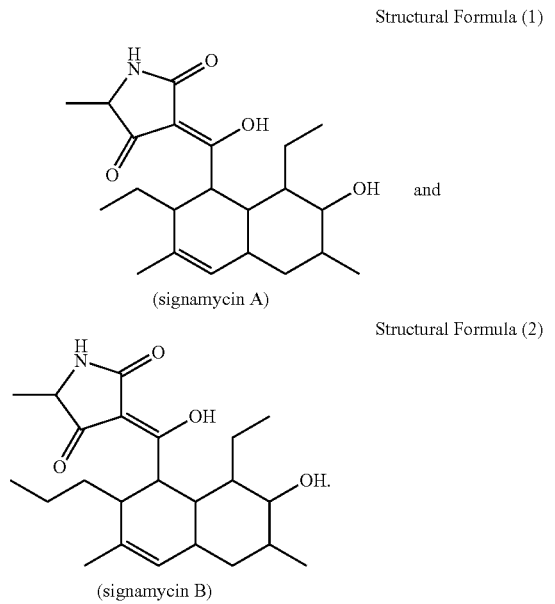

(signamycin A)

Structural Formula (2)

(signamycin B)

6. An enzyme activity inhibitor comprising: at least one of a compound selected from the group consisting of a compound having a structure expressed by following Structural Formula (1) and a compound having a structure expressed by following Structural Formula (2):

Structural Formula (1)

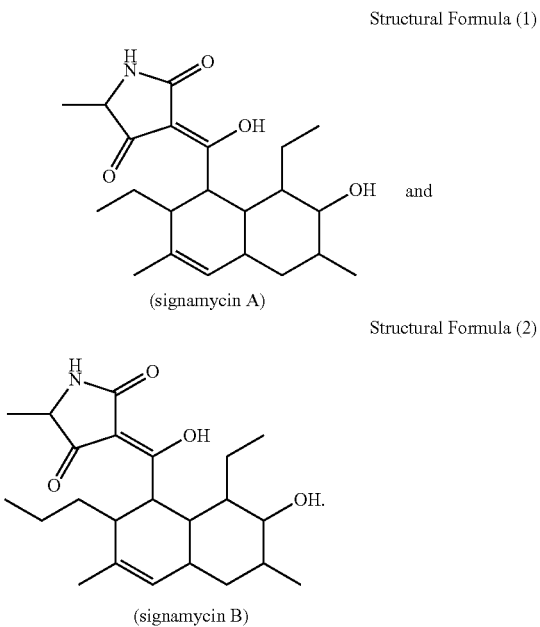

(signamycin A)

Structural Formula (2)

(signamycin B)

* * * * *